United States Patent [19]
Greenhaff et al.

[11] Patent Number: 5,968,900
[45] Date of Patent: Oct. 19, 1999

[54] INCREASING CREATINE AND GLYCOGEN CONCENTRATION IN MUSCLE

[75] Inventors: Paul Leonard Greenhaff, Wollaton; Allison Lesley Green, The Park; Ian Andrew MacDonald, Beeston, all of United Kingdom; Eric Hultman, Stockholm, Sweden

[73] Assignee: The University of Nottingham, Nottingham, United Kingdom

[21] Appl. No.: 08/875,326

[22] PCT Filed: Dec. 15, 1995

[86] PCT No.: PCT/GB95/02933

§ 371 Date: Sep. 29, 1997

§ 102(e) Date: Sep. 29, 1997

[87] PCT Pub. No.: WO96/18313

PCT Pub. Date: Jun. 20, 1996

[30] Foreign Application Priority Data

Aug. 25, 1995 [GB] United Kingdom .................. 9517443

[51] Int. Cl.$^6$ .......................... A61K 38/28; A61K 31/70; A61K 31/715; A61K 31/195
[52] U.S. Cl. .................................. 514/3; 514/4; 514/23; 514/53; 514/54; 514/565
[58] Field of Search .............................. 514/3, 4, 23, 53, 514/54, 565

[56] References Cited

FOREIGN PATENT DOCUMENTS

| 0 449 787 | 2/1991 | European Pat. Off. . |
| WO94/02127 | 3/1994 | WIPO . |

OTHER PUBLICATIONS

Anon, Pschyrembel –Klinisches Wortberbuch, 1990, Walter de Gruyter, Berlin–New York (1990), pp. 790–792; 902–903.

Haider W. Et al., "Improvement of Cardiac Preservation by Preoperative High Insulin Supply," Database Embase, Elsevier Science Publishers, Amsterdam, NL, J. Thorac, Cardiovasc. Surg. (1984).

Samuel P. Bessman, "The Oringin of theCreatine–Creatine Phosphate Energy Shuttle", pp. 75–81, Heart Creatine Kinase–Chapter 7(1980) .

*Primary Examiner*—Kimberly Jordan
*Attorney, Agent, or Firm*—Watts, Hoffmann, Fisher & Heinke Co., L.P.A.

[57] ABSTRACT

Compositions herein increased creatine retention and/or glycogen storage in muscle. A composition comprises creatine or its derivative and a carbohydrate or its derivative. The carbohydrate is in an amount by weight which is greater than the amount of creatine. The amount of carbohydrate and the amount of creatine are effective for increasing creatine retention and/or glycogen storage in muscle. The compositions may be in the form of a pharmaceutical or a dietary supplement and are intended for use in the human or animal body. Other compositions comprise creatine or an active derivative together with insulin or an active derivative. The amount of creatine and the amount of insulin are effective for increasing creatine retention and/or glycogen storage in muscle. The compositions including creatine and insulin may further contain a carbohydrate or its derivative. A method of increasing creatine retention in a human or animal body comprises causing an increase in blood plasma creatine concentration and causing a substantially simultaneous increase in blood plasma insulin concentration. A method of increasing glycogen storage in a human or animal body comprises causing an increase in blood plasma creatine carbohydrate concentration and causing a substantially simultaneous increase in blood plasma creatine concentration. The compositions to increase the creatine retention and/or glycogen storage in the muscle are administered by injection or ingestion.

53 Claims, 3 Drawing Sheets

INCREASING CREATINE AND GLYCOGEN CONCENTRATION IN MUSCLE

This is a 371 of PCT/6B95/02933, filed Dec. 15, 1995.

The present invention concerns the retention of creatine within the body, and relates in particular but not exclusively to a method and composition for increasing creatine uptake in humans. The invention also concerns a method and composition for simultaneously increasing glycogen concentration in muscle.

Creatine (methylglycocyamine, $H_2NC=NH \cdot N(CH_3)CH_2CO_2H$) is known to be present in the muscles of vertebrates. It is present in a phosphorylated and a non-phosphorylated form and has been shown to be involved in muscular contraction and the development of fatigue. Creatine is produced naturally by the body, but is also obtained from animal foods.

Most bodily creatine is present in muscle, and it is believed that increasing the amount of creatine within muscle favorably affects muscular performance and the amount of work which can be done by the muscle. Accordingly, it is held desirable to be able to influence creatine retention in the body.

Glycogen, $(C_6H_{10}O)x$, is a carbohydrate found in animal cells and is convertible from and to glucose. Athletes endeavour to increase muscle glycogen content before competing in order to enhance muscle performance.

In this specification the term "active derivative" means anything derived from or a precursor of the relevant substance that acts in the same or similar way in the body to the substance, or which is processed into the substance when placed into the body. The terms serum and plasma can be interchanged.

According to the invention there is provided a method of increasing creatine retention in the human or animal body by causing an increase in blood plasma creatine concentration and causing a substantially simultaneous increase in blood plasma insulin concentration.

The plasma creatine concentration may be increased by ingestion and/or in fusion of creatine or an active derivative thereof.

The plasma insulin concentration may be increased by infusion of insulin or an active derivative thereof and/or by the ingestion of an agent operable to cause an increase in the blood plasma insulin concentration.

The agent may be a carbohydrate or an active derivative thereof, preferably a simple carbohydrate. Preferably the carbohydrate is glucose.

Preferably the method comprises the simultaneous ingestion of creatine and an agent operable to cause an increase in the blood plasma insulin concentration substantially simultaneously with the arrival in the plasma of the creatine.

The creatine and/or the agent is preferably orally ingested.

The invention further provides a method of increasing glycogen storage, and particularly glycogen concentration in muscle of the human or animal body by causing an increase in blood plasma carbohydrate concentration and insulin concentration and causing a substantially simultaneous increase in blood plasma creatine concentration.

The plasma creatine concentration may be increased by ingestion and/or infusion of creatine or an active derivative thereof. The plasma carbohydrate, which is desirably glucose and insulin concentrations may be increased by ingestion of carbohydrate or an active derivative thereof, but desirably glucose and/or any other simple carbohydrate and/or by infusion of a carbohydrate or an active derivative thereof, such as glucose or any other simple carbohydrate.

Preferably creatine or an active derivative thereof and glucose and/or another simple carbohydrate are orally ingested.

According to the invention there is further provided a composition for increasing creatine retention in the human or animal body, the composition comprising creatine or an active derivative thereof together with a carbohydrate or an active derivative thereof.

Preferably the composition is in the nature of a dietary supplement.

Preferably the carbohydrate is glucose and/or another simple carbohydrate.

The composition preferably comprises 2 to 8% by weight creatine and 92 to 98% by weight glucose and/or another simple carbohydrate.

According to the invention there is also provided a method of increasing creatine retention in the human or animal body by ingestion and/or injection of a composition as hereinbefore described. Preferably the composition is ingested in an amount of 100 g to 700 g per day. Which may be taken in four equal parts throughout the day.

Further according to the present invention there is provided a composition for increasing creatine retention in the human or animal body, the composition comprising creatine or an active derivative thereof together with insulin or an active derivative thereof.

Further according to the present invention there is provided a composition for increasing glycogen storage in the human or animal body and particularly glycogen concentration in muscle, the composition comprising creatine or an active derivative thereof together with insulin or an active derivative thereof.

The composition may be in a form to be ingested and/or injected into the body.

According to the invention there is also provided a method of increasing creatine retention in the human or animal body by ingestion and/or injection of a composition as described above.

According to a further aspect of the invention there is provided a method increasing glycogen storage in the human or animal body and particularly glycogen concentration in muscle by ingestion and/or injection of a composition as described above.

Preferably a carbohydrate, or an active derivative thereof, is also ingested and/or injected desirably such that an increase in blood plasma carbohydrate concentration and insulin concentration occurs substantially simultaneously with an increase in blood plasma creatine concentration.

According to the invention there is also provided a composition for increasing glycogen storage in the animal or human body and particularly glycogen concentration in muscle of the human or animal body, the composition comprising creatine or an active derivative thereof together with a carbohydrate or an active derivative thereof.

Preferably the composition is in the nature of a dietary supplement.

Preferably the carbohydrate is glucose and/or another simple carbohydrate.

The composition preferably comprises 2 to 8% by weight creatine and 92 to 98% by weight glucose and/or another simple carbohydrate.

According to the invention there is also provided a method of increasing glycogen storage in the human or animal body and particularly glycogen concentration in muscle by ingestion and/or injection of a composition as hereinbefore described.

Preferably the composition is ingested in an amount of 100 g to 700 g per day, which may be taken in four equal parts throughout the day.

According to the invention there is further provided a composition comprising creatine or an active derivative thereof and a carbohydrate or an active derivative thereof for use as an active pharmaceutical composition.

The invention also provides a composition comprising creatine or an active derivative thereof and insulin or an active derivative thereof for use as an active pharmaceutical preparation. The composition may also comprise a carbohydrate or an active derivative thereof.

The invention further provides creatine or an active derivative thereof and a carbohydrate or an active derivative thereof for use in the manufacture of a substance for increasing creatine retention in the human or animal body.

The invention also provides a composition comprising creatine or an active derivative thereof, and insulin or an active derivative thereof, for use in the manufacture of a substance for increasing creatine retention and/or glycogen storage in the human or animal body, such as muscle. Carbohydrate or an active derivative thereof may also be provided.

The invention further provides a composition comprising creatine or an active derivative thereof and a carbohydrate or an active derivative thereof for use in the manufacture of a substance for increasing glycogen concentration in muscle of the human or animal Preferably the carbohydrate is glucose and/or another simple carbohydrate.

The composition preferably comprises 2 to 8% by weight creatine and 92 to 98% by weight glucose and/or another simple carbohydrate.

The methods and compositions of the invention may be used to increase bodily creatine retention in humans. This is desired, for example, by sportsmen and athletes to avoid or delay the onset of muscular fatigue. The ability to increase creatine retention may also be desired in individuals having relatively low general creatine levels, for example vegetarians who do not take animal protein, and sufferers of disease which affects muscle. The present invention enables creatine retention to be increased to a greater extent than is achieved by making creatine available to the body alone.

The invention also permits the increase of muscle glycogen concentration. This is desired by athletes to enhance performance. Also, increasing the glycogen concentration in muscle is of interest where insulin sensitivity of the body is impaired by, for example, obesity, diabetes, heart failure or post-surgical trauma.

BRIEF DESCRIPTION OF THE DRAWINGS

The invention will be further described for the purposes of illustration only with reference to the following examples and to the drawings, in which.

EXAMPLE 1

Experimental 16 men were randomly divided into groups 1 (6 members), 2 (6 members) and 3 (4 members). On day one, fasted subjects gave a blood sample and then consumed the following preparations:

Group 1–5 g creatine in 250 ml low calorie hot orange

Group 2–5 g creatine in 250 ml low calorie hot orange plus 500 ml of a glucose drink (LUCOZADE(™) manufactured by Smith Kline Beecham), containing 90–100 g simple sugars.

Group 3–250 ml of low calorie hot orange

Arterialized-venous blood samples were then obtained at 20 minute intervals for the next 4½ hours, while subjects remained in a supine position. For the remainder of the day, and throughout day two, subjects ingested the mentioned preparations at 4 hourly intervals, representing a total daily creatine dose of 20 g. On the morning of day three the subjects reported back to the laboratory and underwent the same procedures as on the first day. All subjects weighed and recorded their dietary intake throughout the study, subjects in group 2 consuming a prescribed high carbohydrate diet, and undertook 24 hour urine collections on day one and day three. Plasma and urine creatine were measured using high performance liquid chromatography and serum insulin was measured using a radioimmunoassay technique.

Results

The results are shown in Table 1, in which CR=creatine. Plasma creatine concentration (u mol/l) was plotted against time for each group, and the area under each curve was determined. Urinary creatine (g) and peak serum insulin (mIU/l) were also determined.

Plasma creatine concentrations peaked within 90 minutes of creatine ingestion and declined towards resting values during the remaining 180 minutes of the 4½ hour period. The area under the plasma creatine curve was lower in group 2 than in group 1, as was urinary creatine content. Following carbohydrate ingestion, serum insulin levels peaked within 30 minutes in group 2 and returned to the pre-ingestion concentration over the remaining 240 minutes. Plasma insulin concentration did not change in group 1 or group 3 over the course of the experiment.

TABLE 1

|  | Group 1 | | Group 2 | |
| --- | --- | --- | --- | --- |
|  | Mean | SE | Mean | SE |
| Day 1 | | | | |
| Area under plasma CR (umol/l/min) | 2834.1 | 298.1 | 883.9$^{++}$ | 109.9 |
| Urinary CR (g) | 9.5 | 1.2 | 5.0* | 0.8 |
| Peak serum insulin (mIU/l) | 7.8 | 1.3 | 72.0$^{++}$ | 11.2 |
| Day 3 | | | | |
| Area under plasma CR (umol/l/min) | 2637.5 | 228.6 | 948.3* | 454.5 |
| Urinary CR (g) | 11.9 | 1.1 | 5.7$^{+}$ | 1.2 |
| Peak serum insulin (mIU/l) | 9.5 | 2.0 | 84.2$^{++}$ | 11.5 |

*$P < 0.05$; $^{+}P < 0.01$; $^{++}P < 0.001$ - significantly different from corresponding value.

The reduced area under the plasma creatine curve and the lower urinary creatine content of those subjects which had ingested creatine and carbohydrate compared with those which had ingested only creatine shows that bodily uptake of creatine is greater in the second group. This increase in creatine uptake is believed to be insulin mediated, the plasma insulin concentration being increased by the ingested carbohydrate.

EXAMPLE 2

Experimental

A muscle biopsy sample was taken from the vastus lateralis muscle of each of 21 healthy males and was frozen in liquid nitrogen for subsequent biochemical analysis. Beginning the following day, 12 subjects (group A) each ingested 5 g of creatine dissolved in hot sugar-free orange juice, four times a day for 5 days. The remaining 9 subjects (group B) proceeded as group A, but in addition consumed 500 ml of LUCOZADE, 30 minutes after each creatine preparation had been ingested. Subjects returned the day after the 5th day of supplementation and further muscle biopsy samples were taken. 24 hour urinary collections were made prior to the first biopsy sample (control) and on the first day of creatine supplementation (day 2). Urinary creatine content (in grams) was then measured using high performance liquid chromatography.

Results

Table 2 shows the muscle concentration (mmol/kg dry mass, mean +S.E.M.) of phosphorylated creatine (PCr) non-phosphorylated creatine (Cr) and total creatine (TCr) before and after creatine supplementation. Significant differences between the groups are indicated by an asterisk $p<0.05$.

TABLE 2

|  | Before Creatine Supplementation | After Creatine Supplementation |
|---|---|---|
| PCr | | |
| Group A | 85.1 ± 2.5 | 92.4 ± 2.1 |
| Group B | 84.4 ± 3.8 | 99.4 ± 2.6* |
| Cr | | |
| Group A | 36.4 ± 1.7 | 49.8 ± 1.5 |
| Group B | 39.0 ± 2.3 | 57.1 ± 3.4* |
| TCr | | |
| Group A | 121.5 ± 3.1 | 142.2 ± 2.6 |
| Group B | 123.4 ± 4.3 | 156.4 ± 5.4* |

The increase in total creatine concentration after supplementation in group B was approximately 60% greater than that in group A. This increase comprises increases in both phosphorylated and non-phosphorylated creatine. Urinary creatine content was greater in group A than in group B on day 2 but there was no difference between the groups on the control day.

These results indicate that carbohydrate ingestion increases uptake of creatine in muscle in man, and to a far greater extent than to that seen when creatine alone is ingested.

EXAMPLE 3

The muscle samples obtained in the study of Example 2 were additionally analysed for muscle glycogen concentration. Muscle samples from a further group C containing 8 subjects were also analysed. This group has followed a similar regime to groups. A and B but ingested a preparation of carbohydrate but no creatine, in the form of 500 ml LUCOZADE, at same times as subjects of Groups A and B.

Table 3 shows the muscle concentration (mmol/kg) of glycogen before and after supplementation, and also the difference in the concentration.

TABLE 3

|  | before supplementation | after supplementation | difference |
|---|---|---|---|
| Group A | | | |
| mean | 364.8 | 366.1 | 1.2 |
| sd | 63.4 | 65.8 | 67.9 |
| se | 19.1 | 19.8 | 20.5 |
| Group B | | | |
| mean | 331.1 | 488.7 | 157.6 |
| sd | 32.5 | 125.4 | 126.8 |
| se | 10.8 | 41.8 | 42.3 |
| Group C | | | |
| mean | 337.5 | 413.3 | 75.8 |
| sd | 37.3 | 55.9 | 33.2 |
| se | 13.2 | 19.8 | 11.7 | sd = standard deviation, se = standard error

Table 3 shows that the mean glycogen difference after supplementation in Group A, who took creatine only, was very small.

Figure 1:
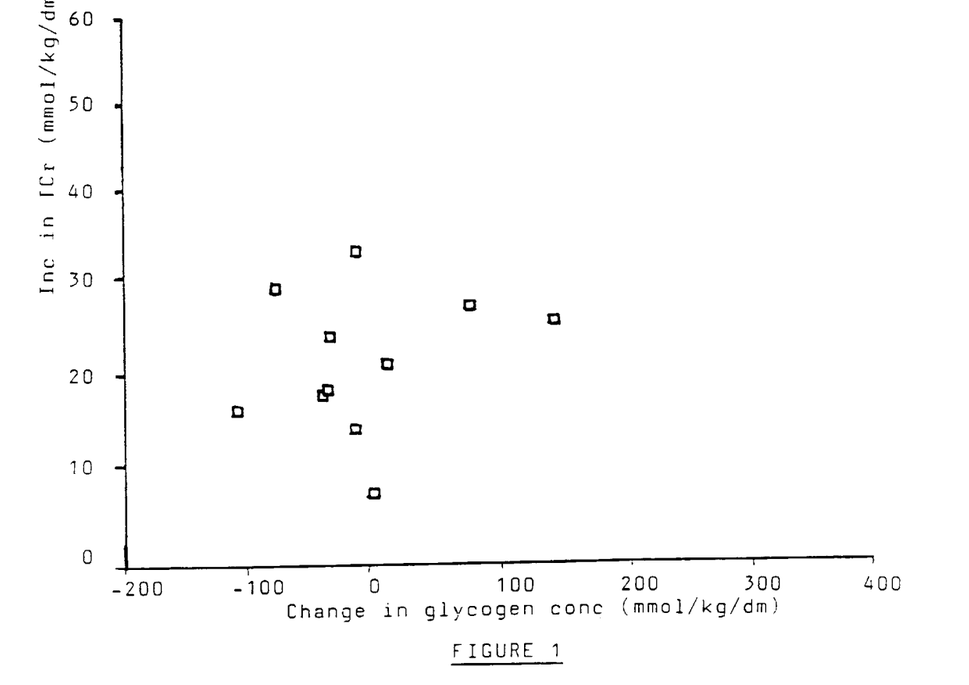
FIG. 1 is a graph showing increase in total creatine concentration against change in glycogen concentration in subjects of group A of Example 2.
Figure 2:
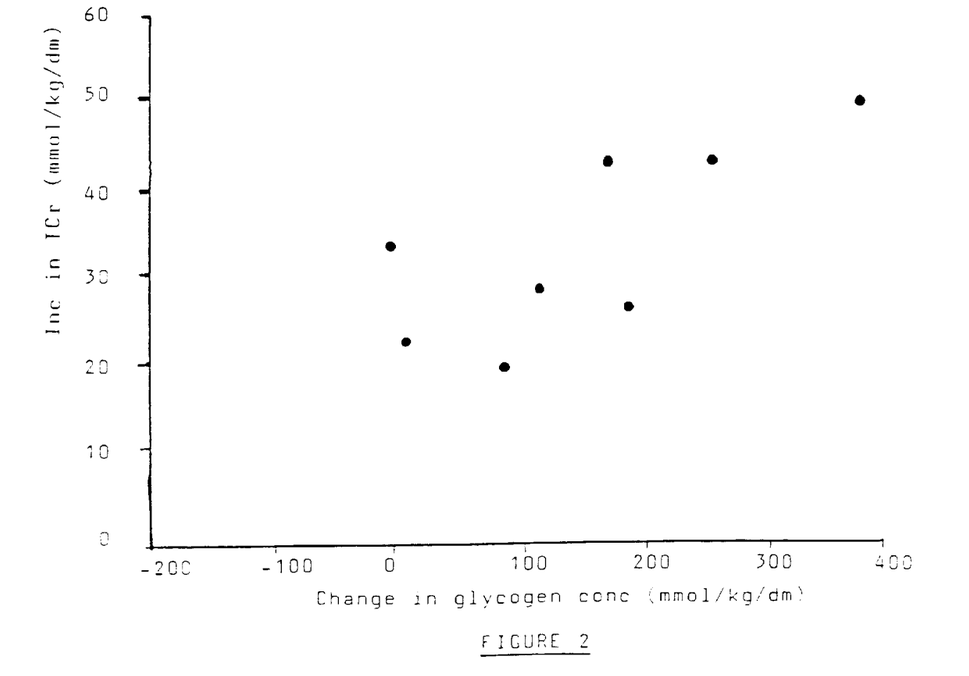
FIG. 2 is a similar graph for subjects of group B of Example 2.

The subjects of Group C, who took glucose only, showed an increase in muscle glycogen concentration after supplementation. However, a more marked increase in muscle glycogen concentration was shown by Group B, who took creatine and glucose together. The results of individual subjects in Group B varied greatly. However, referring to FIG. 2 it is shown that there was a linear relationship between the increase in creatine concentration and the increase in glycogen concentration in subjects of this group, showing a synergistic effect. No such relationship was observed in the subjects in Group A, who ingested only creatine (FIG. 1).

EXAMPLE 4

Experimental

Twenty nine fasted subjects were divided randomly into three groups, group A (12 subjects), group B (9 subjects) and group C (8 subjects). Each member of group A ingested 5 g of creatine dissolved in hot sugar-free orange juice. Each member of group B ingested 5 g of creatine dissolved in hot sugar-free orange juice along with 500 ml of LUCOZADE, 30 minutes after the creatine preparation had been ingested. Group C ingested 500ml of LUCOZADE alone.

Figure 3:
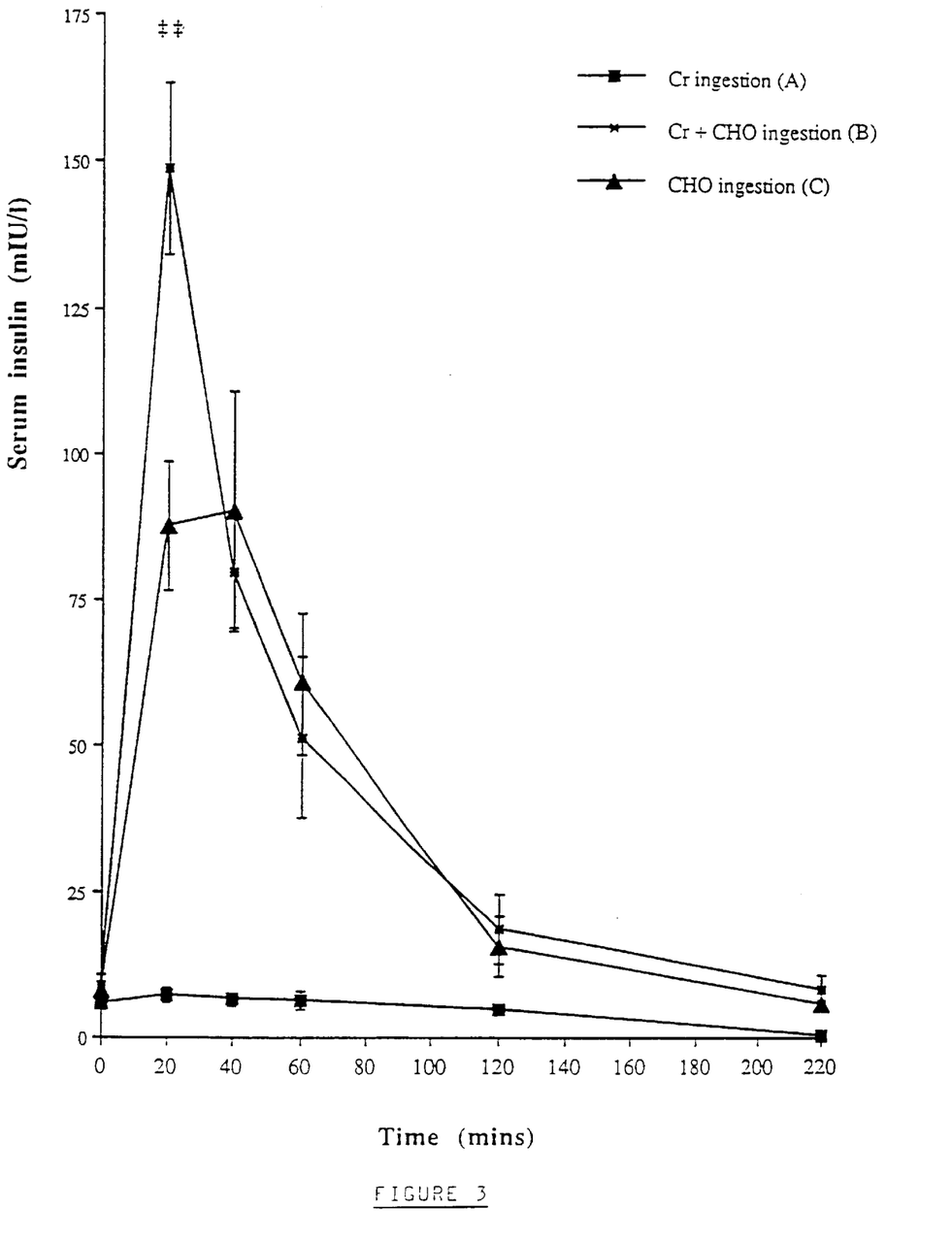
FIG. 3 is a graph showing serum insulin concentration against time for all groups in Example 4.

Arterialised-venous blood samples were obtained from each member of each group before ingestion and at 20 minute intervals immediately following ingestion for the following 220 minutes, while subjects remained in a supine position. Blood serum insulin concentration was measured in each sample, and the results are shown in Table 4 below. Serum insulin concentration (mIU/l) was plotted against time (mins) for each group and is shown in FIG. 3.

Figure 4:
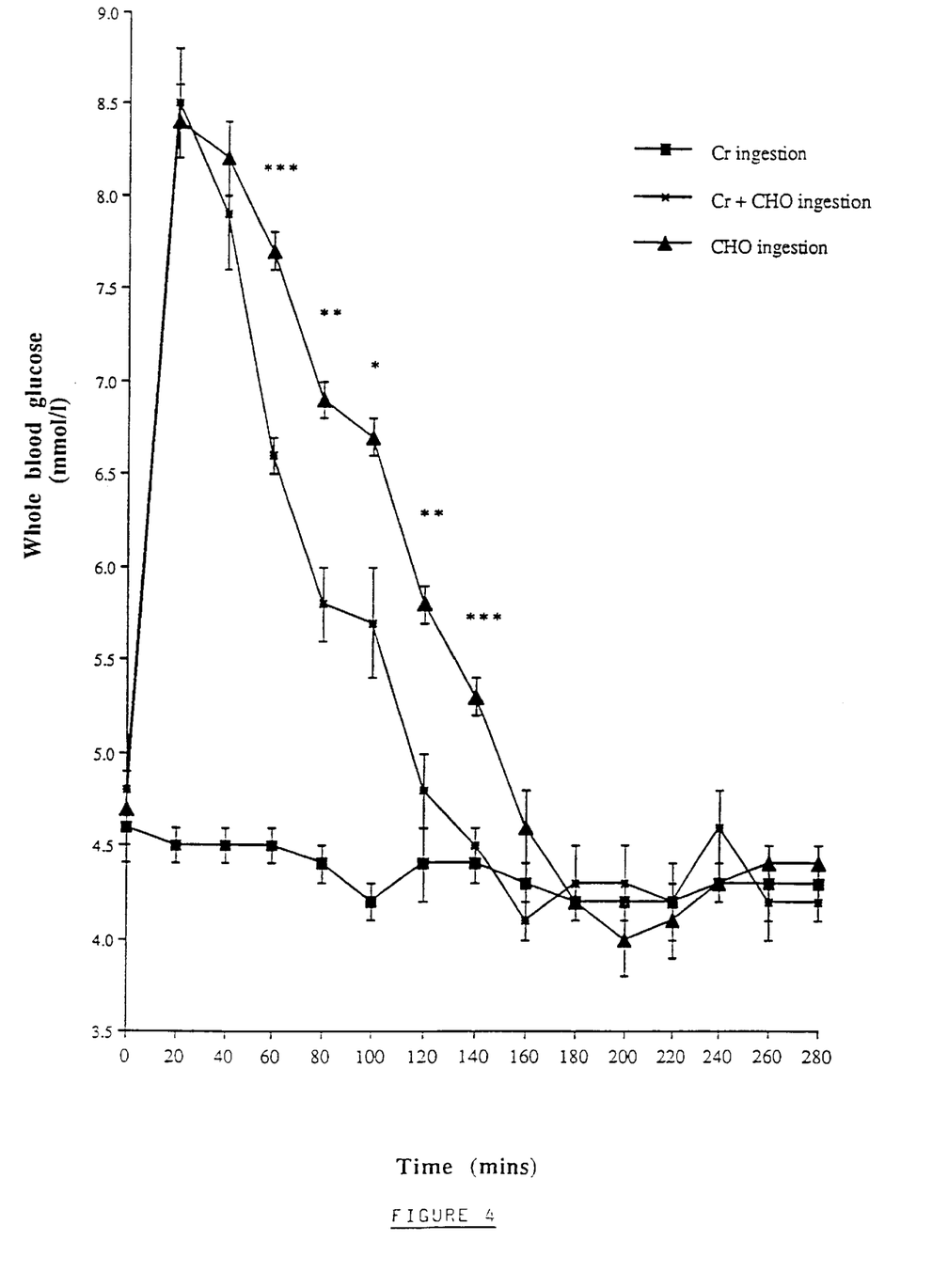
FIG. 4 is a graph showing blood plasma glucose concentration against time, for all groups in Example 4.

The whole blood glucose concentration was also measured before ingestion and at 20 minute intervals for the following 280 minutes and the results obtained are shown in Table 5 below. Whole blood glucose (mmol/l) was plotted against time (mins) for each group and is shown in FIG. 4.

TABLE 4

Plasma Insulin (mIU/l, mean ± SEM)

| Gp | Time (min) | 0 | 20 | 40 | 60 | 120 | 220 |
|---|---|---|---|---|---|---|---|
| A | Creatine | 5.8 ± 0.8 | 7.3 ± 1.2 | 6.5 ± 1.0 | 6.3 ± 1.6 | 4.7 ± 0.3 | 4.7 ± 0.4 |
| B | Creatine + carbohydrate | 8.8 ± 2.0 | 148.7 ± 14.7 | 79.7 ± 9.3 | 51.5 ± 13.7 | 18.6 ± 6.0 | 8.2 ± 2.4 |
| C | Carbohydrate | 8.0 ± 1.5 | 87.6 ± 11.1 | 90.2 ± 20.4 | 60.8 ± 12.1 | 15.6 ± 5.2 | 5.8 ± 0.5 |

TABLE 5

Plasma Glucose (mmol/l, mean ± SEM)

| Gp | Time (min) | 0 | 20 | 40 | 60 | 80 | 100 |
|---|---|---|---|---|---|---|---|
| A | Creatine | 4.6 ± 0.2 | 4.5 ± 0.1 | 4.5 ± 0.1 | 4.5 ± 0.1 | 4.4 ± 0.1 | 4.2 ± 0.1 |
| B | Creatine + carbohydrate | 4.8 ± 0.2 | 8.5 ± 0.3 | 7.9 ± 0.2 | 6.6 ± 0.1 | 5.8 ± 0.5 | 5.7 ± 0.3 |
| C | Carbohydrate | 4.7 ± 0.2 | 8.4 ± 0.2 | 8.2 ± 0.2 | 7.7 ± 0.1 | 6.9 ± 0.0 | 6.7 ± 0.1 |

| Gp | Time (min) | 120 | 140 | 160 | 180 | 200 | 220 | 240 | 280 |
|---|---|---|---|---|---|---|---|---|---|
| A | Creatine | 4.4 ± 0.2 | 4.4 ± 0.1 | 4.3 ± 0.1 | 4.2 ± 0.1 | 4.2 ± 0.1 | 4.2 ± 0.2 | 4.3 ± 0.1 | 4.3 ± 0.1 |
| B | Creatine + carbohydrate | 4.8 ± 0.2 | 4.5 ± 0.1 | 4.1 ± 0.1 | 4.3 ± 0.2 | 4.3 ± 0.2 | 4.2 ± 0.2 | 4.6 ± 0.2 | 4.2 ± 0.1 |
| C | Carbohydrate | 5.8 ± 0.1 | 5.3 ± 0.3 | 4.6 ± 0.2 | 4.2 ± 0.1 | 4.0 ± 0.2 | 4.1 ± 0.2 | 4.3 ± 0.1 | 4.4 ± 0.1 |

The results shown in Table 4 and FIG. 3 clearly show that when creatine is ingested along with carbohydrate (group B), the serum insulin concentration is considerably greater than that found when creatine (group A) and carbohydrate (group C) are ingested alone.

Further, the results shown in Table 5 and FIG. 4, clearly show that when creatine and carbohydrate (group B) are ingested together, there is a considerably more rapid decline in blood plasma glucose concentration, than when carbohydrate is ingested alone. This is a direct result of the augmented release of insulin into the blood caused by the ingested creatine and glucose composition.

This rapid decline in blood plasma glucose concentration is indicative of an increased uptake of glucose into muscle for glycogen synthesis (as seen in Example 3). In other words, the ingestion, or infusion, of creatine in conjunction with carbohydrate increases muscle glycogen storage.

Modifications may be made within the scope of the invention. In particular the carbohydrate may be varied. for example by the use of another simple carbohydrate such as a di-or trisaccharide, although glucose is preferred because of the rapidity with which it enters the bloodstream after ingestion, causing substantially simultaneous peaks in blood insulin and creatine concentrations, and to maximise plasma insulin increase. The creatine, glucose and/or insulin or active derivatives of any of these may be infused into the blood in any suitable manner, for example by injection.

Further, the carbohydrate may be substituted or accompanied by insulin or an active derivative thereof. Ingestion or injection of compositions comprising creatine (or an active derivative thereof) and insulin (or an active derivative thereof) may be complimented by ingestion of carbohydrate, such as glucose, for example in the form of a drink. The timing of ingestion or injection (infusion) of the composition and carbohydrate is such that the increase in blood plasma carbohydrate concentration and insulin concentration and plasma creatine concentration peak substantially simultaneously.

Whilst endeavouring in the foregoing Specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. A method of increasing creatine retention in a human or animal body comprising causing an increase in blood plasma creatine concentration and causing a substantially simultaneous increase in blood plasma insulin concentration.

2. The method according to claim 1 comprising increasing the plasma creatine concentration by ingestion of creatine or an active derivative thereof.

3. The method according to claim 1 comprising increasing the plasma creatine concentration by infusion of creatine or an active derivative thereof.

4. The method according to claim 1 comprising increasing the plasma insulin concentration by infusion of insulin or an active derivative thereof.

5. The method according to claim 1 comprising increasing the plasma insulin concentration by ingestion of an agent operable to cause an increase in the blood plasma insulin concentration.

6. The method according to claim 5 wherein the agent is a carbohydrate or an active derivative thereof.

7. The method according to claim 5 wherein the agent is a simple carbohydrate.

8. The method according to claim 7 wherein the simple carbohydrate is glucose.

9. The method according to claim 5 wherein at least one of the creatine and the agent is orally ingested.

10. The method according to claim 1 comprising increasing the blood plasma creatine concentration by administering creatine or an active derivative thereof and increasing the blood plasma insulin concentration by administering a carbohydrate or an active derivative thereof, wherein the composition comprises the carbohydrate or its derivative in an amount by weight which is greater than an amount of the creatine or its derivative.

11. The method according to claim 10 wherein the composition comprises, in % by weight based upon a total weight of the composition: the creatine or its derivative present in an amount ranging from 2 to 8% and the carbohydrate or its derivative present in an amount ranging from 92 to 98%.

12. The method according to claim 1 comprising ingesting creatine and an agent operable to cause an increase in the blood plasma insulin concentration substantially simultaneously with the arrival in the plasma of the creatine.

13. A method of increasing glycogen storage in a human or animal body comprising causing an increase in blood plasma carbohydrate concentration and insulin concentration and causing a substantially simultaneous increase in blood plasma creatine concentration.

14. The method according to claim 13 comprising increasing the plasma creatine concentration by administering creatine or an active derivative thereof by at least one of ingestion and infusion.

15. The method according to claim 13 comprising increasing the plasma carbohydrate and insulin concentrations by administering a carbohydrate or an active derivative thereof by at least one of ingestion and infusion.

16. The method according to claim 13 comprising increasing the plasma glucose and insulin concentrations by infusion of a carbohydrate or an active derivative thereof, the carbohydrate being selected from the group consisting of glucose and other simple carbohydrates.

17. The method according to claim 13 comprising orally ingesting creatine or an active derivative thereof and a carbohydrate or an active derivative thereof, the carbohydrate being selected from the group consisting of glucose and other simple carbohydrates.

18. The method according to claim 13 comprising increasing the blood plasma creatine concentration by administering creatine or an active derivative thereof and increasing the blood plasma insulin concentration by administering a carbohydrate or an active derivative thereof, wherein the composition comprises the carbohydrate or its derivative in an amount by weight which is greater than an amount of the creatine or its derivative.

19. The method according to claim 18 wherein the composition comprises, in % by weight based upon a total weight of the composition: the creatine or its derivative present in an amount ranging from 2 to 8% and the carbohydrate or its derivative present in an amount ranging from 92 to 98%.

20. A composition for use in a human or animal body, the composition comprising creatine or an active derivative thereof together with a carbohydrate or an active derivative thereof, wherein the composition comprises the carbohydrate or its derivative in an amount by weight which is greater than an amount of the creatine or its derivative, and the amount of the creatine or its derivative and the amount of the carbohydrate or its derivative are effective to increase creatine retention in the body.

21. The composition according to claim 20 wherein the composition is in the nature of a dietary supplement.

22. The composition according to claim 20 wherein the carbohydrate is selected from the group consisting of glucose and other simple carbohydrates.

23. The composition according to claim 20 wherein the composition comprises in % by weight based upon a total weight of the composition: the creatine or its derivative present in an amount ranging from 2 to 8% and the carbohydrate or its derivative present in an amount ranging from 92 to 98%.

24. The composition according to claim 20 wherein the amount of the creatine or its derivative and the amount of the carbohydrate or its derivative are effective to increase glycogen storage in the body.

25. A method of increasing creatine retention in a human or animal body comprising administering a composition comprising creatine or an active derivative thereof together with a carbohydrate or an active derivative thereof by at least one of ingestion and injection, wherein the composition comprises the carbohydrate or its derivative in an amount by weight which is greater than an amount of the creatine or its derivative.

26. The method according to claim 25 wherein the composition is ingested in an amount of 100 g to 700 g per day.

27. The method according to claim 25 wherein the composition is administered in four equal parts throughout the day.

28. The method according to claim 25 wherein the composition comprises, in % by weight based upon a total weight of the composition: the creatine or its derivative present in an amount ranging from 2 to 8% and the carbohydrate or its derivative present in an amount ranging from 92 to 98%.

29. The method of claim 25 wherein the carbohydrate is selected from the group consisting of glucose and other simple carbohydrates.

30. A composition for use in a human or animal body comprising creatine or an active derivative thereof together with insulin or an active derivative thereof.

31. The composition according to claim 30 wherein the creatine or its derivative and the insulin or its derivative are present in amounts effective to increase glycogen storage in the body.

32. The composition according to claim 30 wherein the creatine or its derivative and the insulin or its derivative are present in amounts effective to increase creatine retention in the body.

33. The composition according to claim 30 wherein the composition is in a form that can be administered by at least one of ingestion and injection.

34. 8 The composition according to claim 30 further comprising a carbohydrate or an active derivative thereof.

35. A method of increasing creatine retention in a human or animal body comprising administering a composition comprising creatine or an active derivative thereof together with insulin or an active derivative thereof by at least one of ingestion and injection.

36. A method according to claim 35 further comprising administering a carbohydrate or an active derivative thereof such that an increase in blood plasma carbohydrate concentration and insulin concentration occurs substantially simultaneously with an increase in blood plasma creatine concentration.

37. A method of increasing glycogen storage in a human or animal body comprising administering a composition comprising creatine or an active derivative thereof together with insulin or an active derivative thereof by at least one of ingestion and injection.

38. A method according to claim 37 further comprising administering a carbohydrate or an active derivative thereof such that an increase in blood plasma carbohydrate concentration and insulin concentration occurs substantially simultaneously with an increase in blood plasma creatine concentrations.

39. A method of increasing glycogen storage in the human or animal body comprising administering a composition comprising creatine or an active derivative thereof together with a carbohydrate or an active derivative thereof by at least one of ingestion and infusion, wherein the composition comprises the carbohydrate or its derivative in an amount by weight which is greater than an amount of the creatine or its derivative.

40. A method according to claim 39 wherein the composition is ingested in an amount of 100 g to 700 g per day.

41. A method according to claim 39 wherein the composition is administered in four equal parts throughout the day.

42. The method according to claim 39 wherein the composition comprises, in % by weight based upon a total weight of the composition: the creatine or its derivative present in an amount ranging from 2 to 8% and the carbohydrate or its derivative present in an amount ranging from 92 to 98%.

43. The method according to claim 39 wherein the carbohydrate is selected from the group consisting of glucose and other simple carbohydrates.

44. A pharmaceutical having a composition comprising creatine or an active derivative thereof together with a carbohydrate or an active derivative thereof, wherein the composition comprises the carbohydrate or its derivative in the amount by weight which is greater than an amount of the creatine or its derivative, and the amount of said creatine or its derivative and the amount of said carbohydrate or its derivative are effective to increase creatine retention in the body.

45. A pharmaceutical having a composition comprising creatine or an active derivative thereof together with insulin or an active derivative thereof.

46. The pharmaceutical according to claim 45 wherein the composition further comprises a carbohydrate or an active derivative thereof in an amount by weight which is greater than an amount of the creatine or its derivative.

47. A composition for use in a human or animal body, the composition comprising creatine or an active derivative thereof together with a carbohydrate an active derivative thereof, wherein the composition comprises the carbohydrate or its derivative in an amount by weight which is greater than an amount of the creatine or its derivative, and the amount of said creatine or its derivative and the amount of said carbohydrate or its derivative are effective to increase glycogen storage in the body.

48. The composition according to claim 47 wherein the composition is in the nature of a dietary supplement.

49. The composition according to claim 47 wherein the carbohydrate is selected from the group consisting of glucose and other simple carbohydrates.

50. The composition according to claim 47, wherein the composition comprises, in % by weight based upon a total weight of the composition: the creatine or its derivative present in an amount ranging from 2 to 8% and the carbohydrate or its derivative in an amount ranging from 92 to 98%.

51. The composition according to claim 47 wherein the amount of said creatine or its derivative and the amount of said carbohydrate or its derivative are effective to increase creatine retention in the body.

52. A pharmaceutical having a composition comprising creatine or an active derivative thereof together with a carbohydrate or an active derivative thereof, wherein the composition comprises the carbohydrate or its derivative in an amount by weight which is greater than an amount of the creatine or its derivative, and the amount of the creatine or its derivative and the amount of the carbohydrate or its derivative are effective to increase glycogen storage in the body.

53. A composition for use in a human or animal body comprises, in % by weight based upon a total weight of the composition: creatine or its derivative present in an amount ranging from 2 to 8% and a carbohydrate or its derivative in an amount ranging from 92 to 98%.

* * * * *

UNITED STATES PATENT AND TRADEMARK OFFICE
CERTIFICATE OF CORRECTION

PATENT NO.: 5,968,900
DATED: October 19, 1999
INVENTOR(S): Paul Leonard Greenhaff It is certified that error appears in the above-identified patent and that said Letters Patent is hereby corrected as shown below:

Title page, item

[30] Foreign Application Priority Data
Aug. 17, 1994 [GB] United Kingdom.....................9425514.8

Signed and Sealed this

Twelfth Day of September, 2000

Attest:

Q. TODD DICKINSON

*Attesting Officer*   *Director of Patents and Trademarks*